(12) United States Patent
Hansis et al.

(10) Patent No.: US 9,269,166 B2
(45) Date of Patent: Feb. 23, 2016

(54) MOTION COMPENSATED IMAGING (75) Inventors: Eberhard Sebastian Hansis, Hamburg (DE); Cristian Lorenz, Hamburg (DE); Tobias Klinder, Uelzen (DE); Sven Kabus, Hamburg (DE); Xiyun Song, Cupertino, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 74 days.

(21) Appl. No.: 14/116,367

(22) PCT Filed: Apr. 26, 2012

(86) PCT No.: PCT/IB2012/052075
§ 371 (c)(1),
(2), (4) Date: Nov. 8, 2013

(87) PCT Pub. No.: WO2012/153219
PCT Pub. Date: Nov. 15, 2012

(65) Prior Publication Data
US 2014/0072194 A1 Mar. 13, 2014

Related U.S. Application Data

(60) Provisional application No. 61/485,136, filed on May 12, 2011.

(51) Int. Cl.
*G06K 9/00* (2006.01)
*G06T 11/00* (2006.01)
(Continued)

(52) U.S. Cl.
CPC .............. *G06T 11/003* (2013.01); *A61B 6/032* (2013.01); *A61B 6/037* (2013.01); *A61B 6/4417* (2013.01);
(Continued)

(58) Field of Classification Search
CPC .......... G06F 19/3437; G06F 17/30247; A61B 6/032; A61B 6/037; A61B 6/4417; A61B 6/5205; A61B 6/5235; A61B 6/5264; A61B 6/5288; G06T 7/0012; G06T 2211/412; G06T 11/003; G06T 11/005
See application file for complete search history.

(56) References Cited

U.S. PATENT DOCUMENTS 6,490,476 B1 12/2002 Townsend et al.
2002/0077546 A1* 6/2002 Aldefeld ................ A61B 5/055
600/424

(Continued)

FOREIGN PATENT DOCUMENTS

WO 2007015199 A2 2/2007
WO 2010048434 A2 4/2010

OTHER PUBLICATIONS

Reyes et al (Model-based respiratory motion compensation for emission tomography image reconstruction; 2007; Phys. Med. Biol.; 52:3579-3600).*

(Continued)

*Primary Examiner* — Amara Abdi (57) ABSTRACT

A method includes performing a motion compensated reconstruction of functional projection data using a patient-adapted motion model, which is generated based on a generic anatomical motion model and imaging data from a structural scan. A system includes a first adapter (202) configured to adapt a generic anatomical model to structural image data, producing an adapted model, a forward projector (204) configured to forward project the adapted model, producing forward projected data, and a second adapter (206) configured to adapt the forward projected data to individual projections of projected data, which is used to generate the structural image data, producing a patient-adapted motion model.

16 Claims, 5 Drawing Sheets

(51) Int. Cl.
  *A61B 6/03*  (2006.01)
  *A61B 6/00*  (2006.01)
  *G06T 7/00*  (2006.01)

(52) U.S. Cl.
  CPC ............. *A61B 6/5235* (2013.01); *A61B 6/5264* (2013.01); *G06T 7/0012* (2013.01); *G06T 11/005* (2013.01); *A61B 6/486* (2013.01); *A61B 6/5205* (2013.01); *A61B 6/5288* (2013.01); *G06T 2211/412* (2013.01)

(56) References Cited

U.S. PATENT DOCUMENTS

| | | | |
|---|---|---|---|
| 2005/0123183 | A1 | 6/2005 | Schleyer et al. |
| 2006/0140482 | A1* | 6/2006 | Koehler ............... G06T 11/006 381/193 |
| 2007/0232903 | A1 | 10/2007 | Hamill |
| 2008/0202200 | A1* | 8/2008 | West ..................... A61B 6/12 731/1.79 |
| 2008/0218510 | A1* | 9/2008 | Grass ................... G06T 11/005 345/419 |
| 2008/0226149 | A1 | 9/2008 | Wischmann et al. |
| 2009/0245457 | A1* | 10/2009 | Takeuchi .............. G06T 11/008 378/8 |
| 2010/0202664 | A1* | 8/2010 | Busch .................. G06T 11/005 382/107 |
| 2010/0278405 | A1* | 11/2010 | Kakadiaris .......... G06F 19/3431 382/131 |
| 2010/0310140 | A1 | 12/2010 | Schneider et al. |
| 2011/0004112 | A1* | 1/2011 | Flohr ................... A61B 5/0456 600/522 |
| 2011/0058717 | A1* | 3/2011 | Dunavent ............. G06T 7/0014 382/128 |

OTHER PUBLICATIONS

Bitarafan, A., et al.; Respiratory Motion Detection and Correction in ECG-Gated SPECT: a New Approach; 2008; Korean J. Radiol.; 9(6)490-497.

Erlandsson, K., et al.; Reduction of CT artifacts due to respiratory motion in a slowly rotating SPECT/CT; 2008; IEEE Trans. on Nuclear Science; M06-57:3775-3778.

Marin, T., et al.; Motion-compensated temporal summation of cardiac gated SPECT images using a deformable mesh model; 2009; IEEE Trans. on Eng. Med. Biol. Soc.; 1:3657-3660.

Qiao, F., et al.; A motion-incorporated reconstruction method for gated PET studies; 2006; Phys. Med. Biol.; 51:3769-3783.

Reyes, M., et al.; Model-based respiratory motion compensation for emission tomography image reconstruction; 2007; Phys. Med. Biol.; 52:3579-3600.

Segars, W. P., et al.; Effect of Respiratory Motion in CT-based Attenuation Correction in SPECT using Different CT Scanners and Protocols; 2005; IEEE Trans. on Nuclear Science; M10-6:2413-2417.

* cited by examiner

MOTION COMPENSATED IMAGING

CROSS REFERENCE TO RELATED APPLICATIONS

This application is a national filing of PCT application Serial No. PCT/IB2012/052075, filed Apr. 26, 2012, published as WO 2012/153219 A1 on Nov. 15, 2012, which claims the benefit of U.S. provisional application Ser. No. 61/485,136 filed May 12, 2011, which is incorporated herein by reference.

FIELD OF THE INVENTION

The following generally relates to motion compensated imaging and is described with particular application to a single photon emission computed tomography (SPECT)/computed tomography (CT) combined imaging system; however, the following is also amenable to other imaging systems such as separate SPECT and CT imaging systems, positron emission (PET)/CT combined or separate imaging systems, SPECT/magnetic resonance (MR) combined or separate imaging systems, PET/MR combined or separate imaging systems, and/or other individual and/or combinations of imaging systems that provide functional and/or structural information.

BACKGROUND OF THE INVENTION

Patient motion such as respiratory or cardiac motion can degrade the image quality and quantitative accuracy of imaging studies such as cardiac SPECT studies. For example, motion blur can lead to an underestimation of SPECT activity and/or to other image artifacts. Such motion has been compensated using motion-compensated SPECT reconstruction. Conventional motion-compensation approaches require an estimation of a motion vector field or motion model of the region of interest.

A simple motion model has been estimated by tracking statistical features like the center of mass of the SPECT activity in SPECT projection data. However, this method yields a very crude model and can only track motion parallel to the plane of each SPECT projection. Alternatively, a statistical model can be used that represents a mean motion pattern averaged over a patient. Unfortunately, such an approach cannot capture patient-specific motion patterns. A more sophisticated motion model can be derived from dynamic CT, e.g., by performing gated reconstruction (respiratory or cardiac) for different motion states and applying elastic registration. However, dynamic CT data may not always be available, and such studies add to the total dose deposited to the patient for the imaging examination.

Another approach employs external devices, such as video cameras, to track and determine respiratory motion. Such approaches typically face two challenges: 1) they only track the motion of the body surface, and there is no direct link between the external motion and the actual non-rigid motion of internal organs; and 2) they add additional cost to the system and consume additional space. Approaches aiming at directly estimating motion from gated SPECT reconstructions may be hindered by the low count statistics and poor image quality of such reconstructions.

In view of the foregoing, there is an unresolved need for other motion compensation approaches.

SUMMARY OF THE INVENTION

Aspects of the present application address the above-referenced matters, and others.

In one aspect, a method performing a motion compensated reconstruction of functional projection data using a patient-adapted motion model, which is generated based on a generic anatomical motion model and imaging data from a structural scan.

In another aspect, a system includes a first adapter configured to adapt a generic anatomical model to structural image data, producing an adapted model, a forward projector configured to forward project the adapted model, producing forward projected data, and a second adapter configured to adapt the forward projected data to individual projections of projected data, which is used to generate the structural image data, producing a patient-adapted motion model.

In another aspect, a computer readable storage medium is encoded with computer readable instructions, which, when executed by a processor of a computing system, causes the system to: perform a motion compensated reconstruction with attenuation correction of at least one of SPECT or PET projection data based on attenuation correction scan data.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
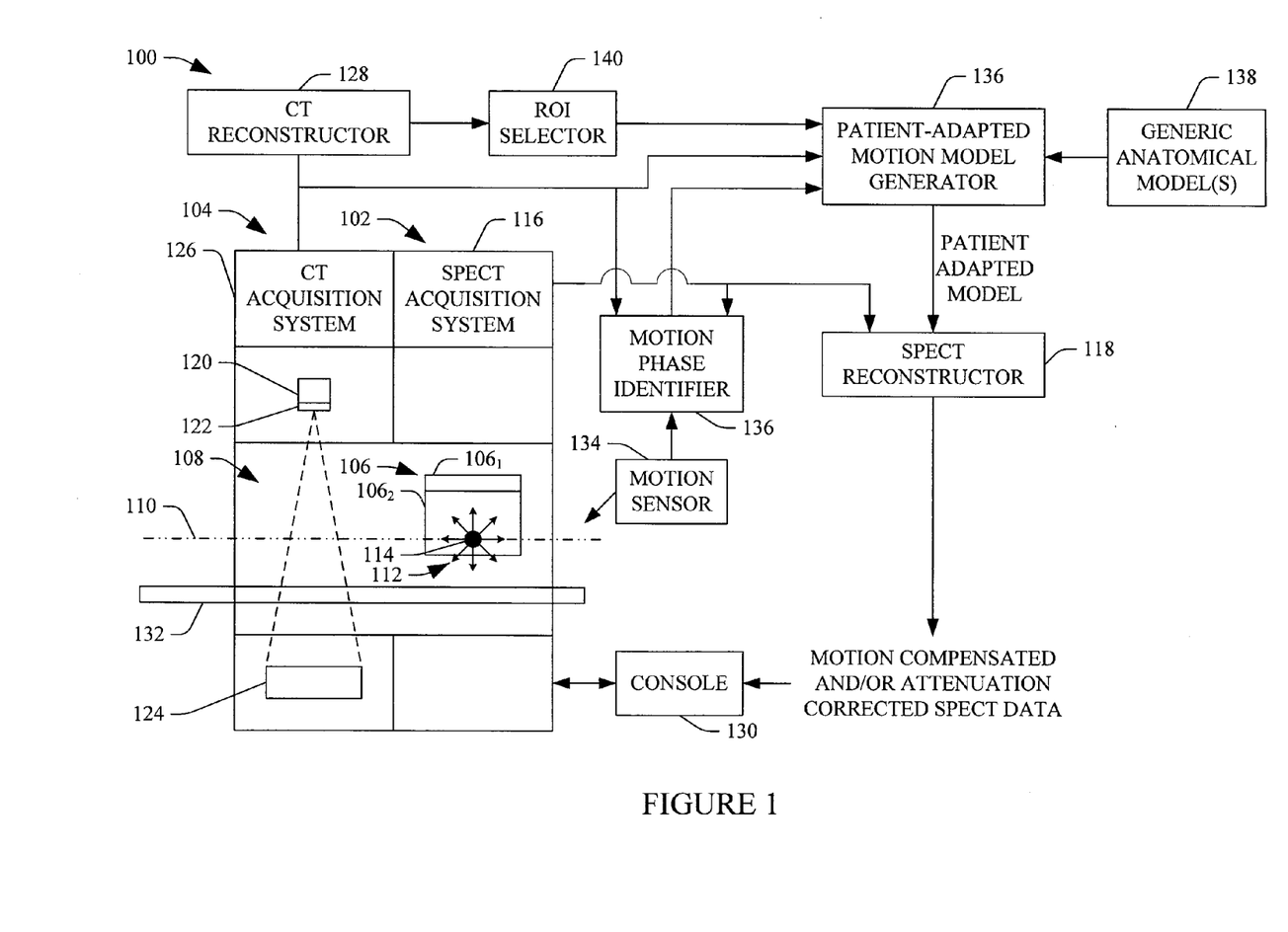
FIG. 1 schematically illustrates an example imaging system in connection with a patient-adapted motion model generator.

FIG. 1 illustrates an imaging system 100, which includes a combined single photon emission computed tomography/computed tomography (SPECT/CT) system with both a SPECT gantry portion 102 and a CT gantry portion 104.

The SPECT portion 102 includes a gamma radiation sensitive detector 106, which, in the illustrated embodiment, includes two detectors $106_1$ and $106_2$ arranged generally perpendicular (e.g., 90° to 102°) to each other. The detector 106 is configured to move tangentially and/or radially with respect to a subject in an examination region 108 and a z-axis 110. The detector 106 detects radiation 112 emitted from decaying radionuclide 114 in the examination region 108 and generates a signal indicative thereof.

A SPECT acquisition system 116 processes the signal and generates SPECT projection data indicative of the detected radionuclide decays. Depending on the implementation, the measured projections may be organized as a plurality of spatial, energy, and/or other bins; the projections may also be presented as list mode data. A SPECT reconstructor 118 reconstructs the SPECT projection data and generates SPECT image data representative of the detected radiation.

In the illustrated embodiment, the SPECT reconstructor 118 can employ a motion compensated reconstruction algorithm, which compensates for patient motion such as pulmonary, cardiac, and/or other patient motion. The SPECT reconstructor 118 additionally or alternatively can employ an attenuation correction algorithm which utilizes attenuation map generated from a CT scan to perform attenuation correction (AC) of the SPECT data.

The CT portion 104 includes a radiation source 120, such as an x-ray tube, that rotates around the examination region 108 about the z-axis 110 and emits radiation towards the examination region 108. A source collimator 122 collimates the emitted radiation. In the illustrated embodiment, the collimator 122 is configured to produce a cone shaped radiation beam that traverses the examination region 108. In other embodiments, the collimator 122 can be configured to produce a fan, wedge, or otherwise shaped beam.

An x-ray radiation sensitive detector 124 detects radiation that traverses the examination region 108 and generates a signal indicative thereof. The illustrated detector 124 includes a two-dimensional large area flat-panel detector. Such a detector may have a large enough detection area to scan an entire or a substantial portion of tissue of interest such as the heart of a patient at a static position without having to move the patient. For example, in one instance, the detection area is about thirty (30) by forty (40) centimeters (cm). In another embodiment, the flat-panel detector is mounted with an offset tangential to the detector trajectory to achieve a large CT field-of-view that enables imaging of the whole body in transaxial direction. In other embodiments, the detector 124 includes a single row or a multiple row of detector array.

A CT acquisition system 126 processes the signal and generates CT projection data indicative of radiation attenuation along a plurality of lines or rays through the examination region 108. A CT reconstructor 128 reconstructs the CT projection data and generates three dimensional (3D) volumetric CT image data. The CT reconstructor 128 can employ various reconstructions algorithms such filtered-backprojection, iterative algorithms, and/or other reconstruction algorithms.

The CT portion 104 can be used to perform an attenuation correction scan in which the resulting data is utilized to perform attenuation correction of SPECT data based on known or other SPECT attenuation correction algorithms. Such a scan may include acquiring data over three hundred and sixty (360) degrees to capture, during free patient respiration, the entire breathing cycle (from full inhalation to full exhalation, or vice versa, over multiple breathing cycles) or a predetermined sub-portion thereof, and may take three hundred (300) seconds to acquire a suitable sampling of motion states from different viewing angles.

A general purpose computer serves an operator console 130. The console 130 includes a human-readable output device such as a monitor or display and an input device such as a keyboard and mouse. Software resident on the console 130 allows the operator to control the operation of the scanner such as selecting a CT attenuation correction scan protocol, a two or three-dimensional CT reconstruction, a motion-compensated SPECT reconstruction with attenuation correction, and/or otherwise interacting with the scanner 100.

A subject support 132 supports a subject or an object in the examination region 110 and allows for moving the subject or the object in x, y and/or z directions with respect to the examination region 110.

A motion sensor 134 is configured to detect motion of moving structure of a subject and generates a motion signal indicative thereof. Examples of moving structure include the heart, the lungs, and/or other moving structure. For cardiac applications, the motion sensor 134 may include an electrocardiograph (ECG), and for respiratory applications, the motion sensor 134 may include a respiratory belt, an optical tracking system using markers attached to the subject, a video camera, etc. In another embodiment, the motion sensor 134 is omitted.

A motion phase identifier 136 identifies a motion phase of different views of the CT and SPECT projection data respectively based on the CT and SPECT projection data and/or the motion signal, and generates motion phase signals indicative thereof.

A patient-adapted motion model generator 136 dynamically generates a patient-adapted motion model (which may be patient specific or general) for a scanned subject based on imaging data (from the subject and/or other subject(s)) and a generic anatomical model(s) 138. For example, in one instance the patient-adapted motion model generator 136 generates the patient-adapted motion model based on CT projection data, reconstructed CT image data (or a portion thereof as identified via a region of interest (ROI) selector 140), the motion signal from the motion phase identifier 136, and the generic anatomical model(s) 138.

As described in further detail below, in one instance, the patient adapted motion model generator 136 generates an accurate patient-adapted motion model for a patient using data from a CT scan used to generate attenuation correction data. As such, the motion model can be generated without exposing the patient to further ionizing radiation such as from an additional scan that is in addition to the CT scan used to generate the attenuation correction data. The motion model can also be used to adapt the attenuation correction data to specific motion phases present in the reconstruction. The dynamically generated patient-adapted motion model can be used by the SPECT reconstructor 118 to motion correct (or mitigate motion effects in) the SPECT data with or without attenuation correction.

It is to be appreciated that the patient adapted motion model generator 136 can be implemented via one or more processors executing one or more computer readable instructions embedded or encoded on computer readable storage medium such as physical memory. Additionally or alternatively, the patient adapted motion model generator 136 can be implemented via the one or more processors executing one or more computer readable instructions carried in a signal and/or carrier wave.

Figure 2:
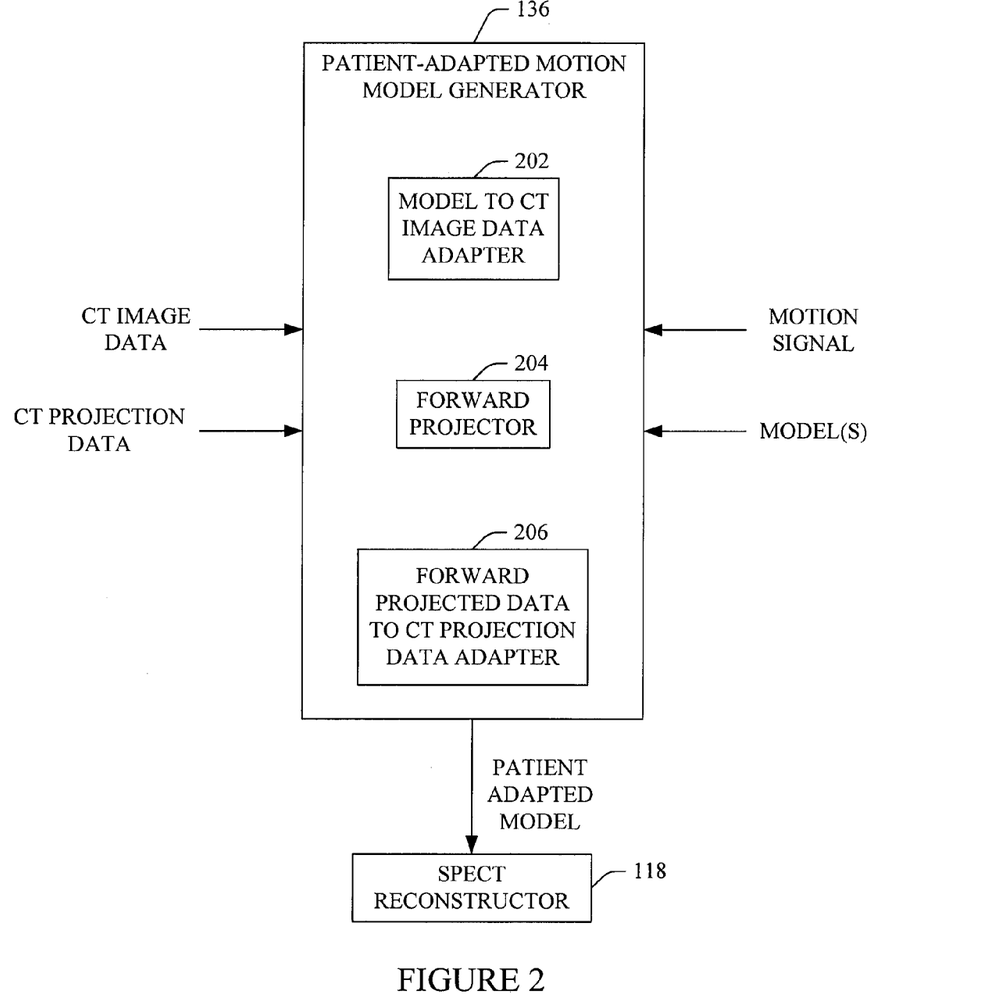
FIG. 2 schematically illustrates an example of the patient-adapted motion model generator.

FIG. 2 schematically illustrates an example of the patient-adapted motion model generator 136. For explanatory purposes, this example is described in connection with respiratory motion. However, it is to be understood that the motion can additionally or alternatively be cardiac motion and/or other patient motion. From FIG. 1, the patient-adapted motion model generator 136 receives as input the model(s) 140, CT projection data, CT image data generated by reconstructing the CT projection data (or a ROI thereof), and the motion signal.

Figure 3:
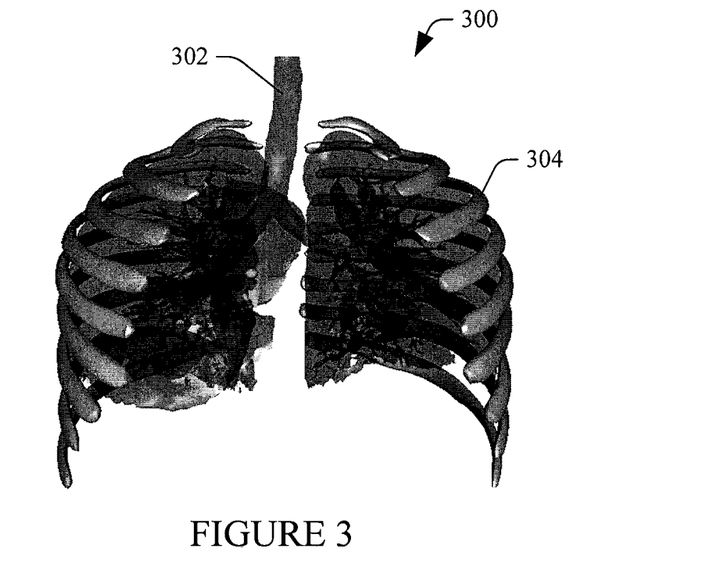
FIG. 3 illustrates an example anatomical surface model including pulmonary structures and the rib cage.
Figure 4:
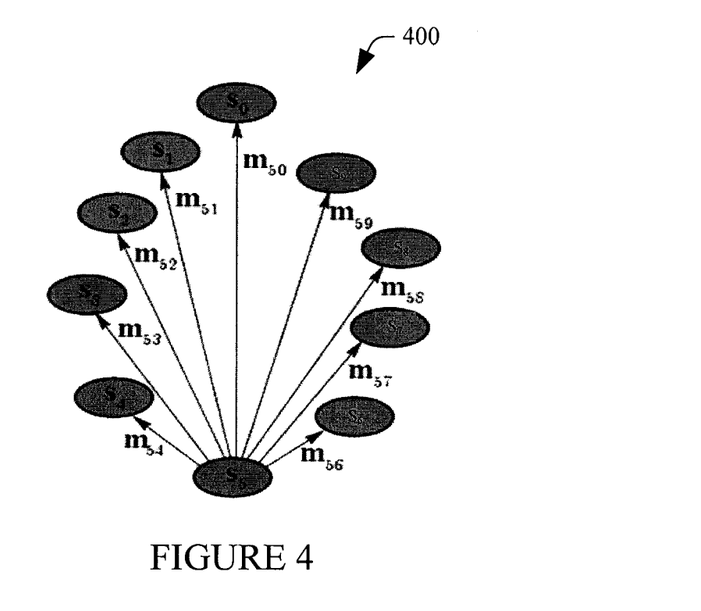
FIG. 4 illustrates an example motion model including displacement vectors for a selected reference motion phase relative to other motion phases.
Figure 5:
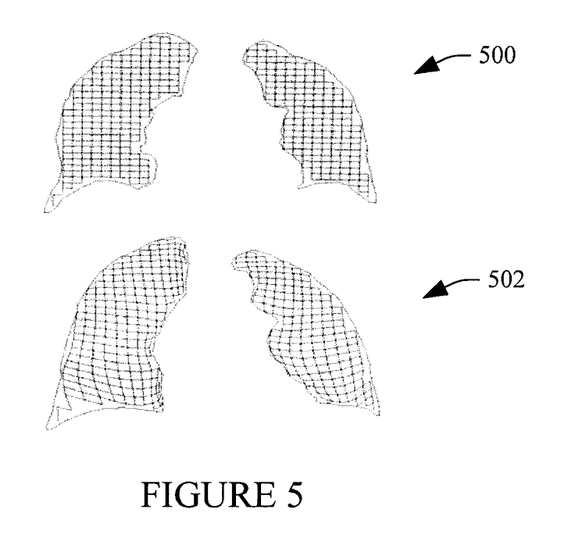
FIG. 5 illustrates displacement vectors on a Cartesian grid, covering the interior of the lungs.
Figure 6:
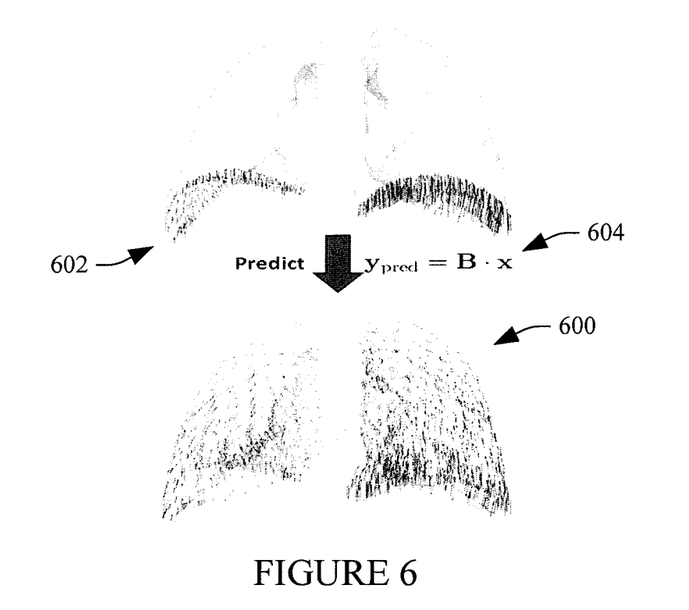
FIG. 6 illustrates estimation of a motion field for the lungs based on motion of the diaphragm.

FIGS. 3-6 show various suitable generic respiratory based models. FIG. 3 illustrates an example of a thorax generic model 300, including a set of surface models of pulmonary structure 302 and the rib cage 304. The surface models can be represented by triangular meshes, covering the lungs and the rib cage, and/or otherwise. FIG. 4 illustrates an example of a motion model 400 describing pulmonary motion of the lungs and surrounding structures. The motion model 400 includes displacement vectors $m_{50}$-$m_{54}$ and $m_{56}$-$m_{59}$ from a selected reference phase $S_5$ to the other breathing phases $S_0$-$S_4$ and $S_6$-$S_9$. Displacement vectors from the reference phase $S_5$ to other phases can be derived from the displacement vectors $m_{50}$-$m_{54}$ and $m_{56}$-$m_{59}$ through interpolation or otherwise. FIG. 5 illustrates models represented by sets of displacement vectors defined on Cartesian grids 500 and 502, both covering the interior of the lungs. FIG. 6 shows an estimation of whole lung motion field 600 based on diaphragm motion 602 using a transformation 604.

Returning to FIG. 2, the patient-adapted motion model generator 136 includes a model to CT image data adapter 202 that adapts or fits the generic models 140 to the 3D CT image data (or a ROI thereof). Generally, the 3D CT image data shows the anatomy in an average motion state. As such, the adapter 202 adapts the model to an average motion state, producing a model that is more patient-adapted than the initial generic model.

In one non-limiting instance, the adapter 202 geometrically adapts the generic model to the 3D CT image data to fit the specific patient anatomy represented in the CT image data. This can be achieved through an organ detection algorithm, leading to a transformation of the model into the patient space, followed by a deformable surface adaptation. With the help of the individualized surface model, the motion model can be transformed into the patient space by a point-based registration and/or other approach.

The patient-adapted motion model generator 136 further includes a forward projector 204 that forward projects the adapted model. The patient-adapted motion model generator 136 further includes a forward projected data to CT projection data adapter 206 that adapts or fits the forward projected data to the CT projection data, producing the patient-adapted model, which takes into account the different motion phases represented in the different acquired projections.

In one non-limiting instance, the adapter 206 dynamically adapts parameters of the model (e.g., inhalation depth, specific motion pattern, etc.) to each (or a sub-set of) the individual respiratory motion state represented by the respective projections of the CT projection data. Generally, each X-ray projection of the AC scan shows the anatomy in a specific motion state. As such, the adapter 206 adapts the model to the individual motion states represented in the CT projection data.

The SPECT reconstructor 118 employs the patient-adapted dynamic model to perform a motion-compensated SPECT reconstruction with or without attenuation correction. Motion-compensated SPECT reconstruction can be performed using known methods, such as motion-compensates filtered-backprojection reconstruction or motion-compensated iterative reconstruction.

Variations are contemplated.

In another embodiment, the SPECT and CT portions respectively are part of separate SPECT and CT imaging systems, which can be located local or remote from each other, such as in different examination rooms.

In still another embodiment, the CT gantry portion 104 is replaced with another imaging modality such as a magnetic resonance (MR) gantry portion.

Additionally or alternatively, the SPECT gantry portion 102 is replaced with another imaging modality such as a positron emission tomography (PET) gantry portion.

The illustrated model adaptation uses knowledge about which motion phase is shown by each projection based on the motion signal. Alternatively, the motion phase can be derived from the projection data by using suitable methods, e.g., tracking the motion of the diaphragm or other anatomical structures in the projection images.

The model adaptation can also make use of the assumption that respiratory motion is periodic.

In another embodiment, the acquired SPECT data is sorted into temporal bins, and the motion phase represented by each bin is derived from, e.g., an external respiration sensor (as shown in FIG. 1), from image-based motion-phase measures such as the center-of-mass of the activity, or from comparing the acquired activity to forward-projections of the dynamic model. For each temporal bin, the anatomic motion state is estimated using the patient-adapted model and the estimated motion phase. The motion state estimate can be further refined by registering the model-based estimate to the gated SPECT projections or a gated SPECT reconstruction.

In another example embodiment, the projection data is acquired such that it contains activity from a plurality of motion states. In this case, the dynamic model can be used to simulate this motion blur during the forward projection and/or backward projection of an iterative reconstruction process. In other words, different motion states of the SPECT activity and AC map are simulated using the motion model and are superimposed in the forward projection, to match the motion blur present in the acquired data. This has been used for myocardial perfusion SPECT and/or other studies.

Figure 7:
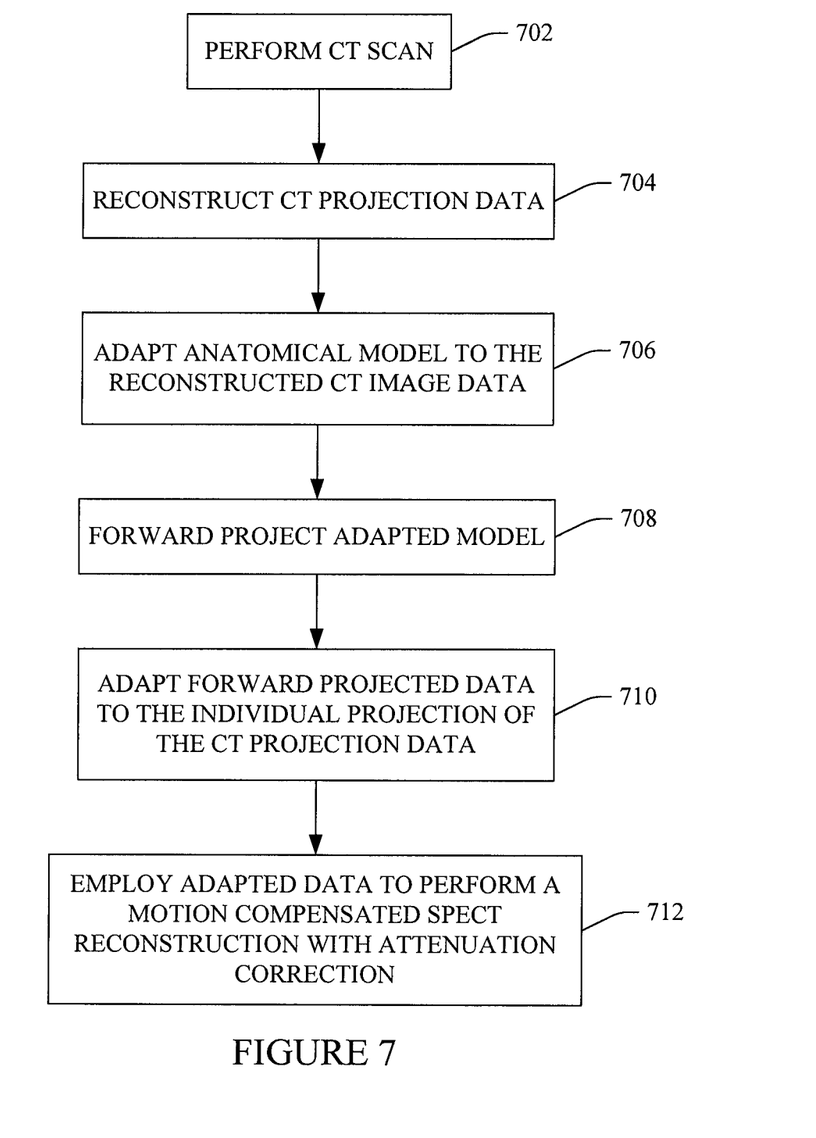
FIG. 7 illustrates an example method.

FIG. 7 illustrates a method in accordance with the description herein.

It is to be appreciated that the ordering of the acts in the methods described herein is not limiting. As such, other orderings are contemplated herein. In addition, one or more acts may be omitted and/or one or more additional acts may be included.

At 702, a CT scan is performed. As described herein, the CT scan can be a SPECT attenuation correction scan or other CT scan.

At 704, the resulting CT projection data is reconstructed, generating volumetric CT image data. As described herein, the resulting reconstructed CT data represents an average motion state (i.e., an average over all the motion phases captured in the scan).

At 706, an anatomical model of tissue of interest is geometrically adapted to the structure in the reconstructed CT image data.

At 708, the adapted model is forward-projected.

At 710, the forward projections are adapted to the individual projections of the CT projection data, producing a dynamically adapted patient-adapted motion model. This can be achieved through similarity, optimization, and/or other algorithms.

At 712, the dynamically adapted patient-adapted motion model is employed for performing a motion compensated SPECT reconstruction with attenuation correction.

The described determination of the motion phase and/or of the anatomic motion state may be refined by registering the CT volume data to the CT projection data or by 2D/3D registration of a SPECT volume to the SPECT projection data. Relative to conventional approaches, the approach described herein can provide a better initial estimate of the motion state to initialize this registration (e.g., from model adaptation to the CT AC scan) which can improve the accuracy and robustness of the registration.

The estimate of the anatomic motion state can then be used to compensate motion in the SPECT reconstruction. The motion estimate can be further used to transform the AC map to the respective motion state, allowing accurate modeling of attenuation and scatter for the respective motion state.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

What is claimed is:

1. A method, comprising:
    geometrically adapting a generic anatomical model to corresponding anatomy represented in image data, producing a patient-adapted anatomical model, and the image data is generated from a CT structural scan which includes at least one entire motion cycle;
    performing a motion compensated reconstruction of functional projection data using the patient-adapted motion model and attenuation correction using the CT structural scan; and
    wherein the at least one entire motion cycle includes free patient respiration from full inhalation to full exhalation to full inhalation, and the patient-adapted anatomical model includes motion displacement vectors for each identified motion phase, and the identified motion phases include a plurality of phases between full inhalation and full exhalation.

2. The method of claim 1, wherein the at least one entire motion cycle includes cardiac and respiratory motion.

3. The method of claim 1, further comprising:
    identifying the motion phases by a sensor.

4. The method of claim 3, wherein the adapting, comprising:
    detecting tissue of interest in the image data;
    transforming the adapted anatomical model to image space; and
    employing a deformable surface adaption to adapt the transformed adapted anatomical model to the detected tissue of interest in the image data.

5. The method of claim 4, wherein the transforming, comprising:
    employing a point-based registration to transform the adapted anatomical model to the image space.

6. The method of claim 1, wherein geometrically adapting includes forward projecting the adapted anatomical model, producing forward projected data, wherein the patient-adapted motion model is generated based on the forward projected data and individual projections from projection data of the CT structural scan.

7. The method of claim 6, further comprising:
    adapting the forward projected data to individual projections of the structural scan, each individual projection representing one of the identified motion states, producing the patient-adapted motion model.

8. The method of claim 7, wherein the functional projection data is sorted into temporal bins, identified by motion phase.

9. The method of claim 8, wherein the motion phase for each bin is derived from at least one of a motion sensor, or image-based motion-phase measures.

10. The method of claim 1, wherein the motion compensated reconstruction includes performing one of a motion-compensated filtered-back projection reconstruction or a motion-compensated iterative reconstruction.

11. A system, comprising:
    a first adapter configured to adapt a generic anatomical model to CT structural image data acquired over at least one entire motion cycle, producing an adapted model;
    a forward projector configured to forward project the adapted model, producing forward projected data;
    a second adapter configured to adapt the forward projected data to individual projections of projection data, which is used to generate the CT structural image data, producing a patient-adapted motion model;
    a reconstructor that utilizes the patient-adapted motion model to motion correct functional projection data and the CT structural image data for attenuation correction of the functional projection data; and
    wherein the at least one entire motion cycle includes free patient respiration from full inhalation to full exhalation to full inhalation, and the patient-adapted anatomical model includes motion displacement vectors for each identified motion phase, and the identified motion phases include a plurality of phases between full inhalation and full exhalation.

12. The system of claim 11, wherein the first adapter geometrically adapts the generic anatomical model to corresponding anatomy represented in the CT structural image data for each identified motion phase, producing an adapted anatomical model.

13. The system of claim 12, wherein the first adapter geometrically adapts the generic anatomical model to corresponding anatomy represented in the CT structural image data through a point-based registration.

14. The system of claim 11, wherein the individual projections of the projection data represent different motion states.

15. The system of claim 11, wherein the functional projection data includes at least one of SPECT or PET data.

16. A non-transitory computer readable storage medium encoded with computer readable instructions, which, when executed by a processor of a computing system, causes the system to:
    perform a motion compensated reconstruction with attenuation correction of at least one of SPECT or PET projection data based on attenuation correction scan data of a CT scan of a patient and a patient-specific motion model generated based on the CT scan that includes at least one entire motion cycle of free patient respiration from full inhalation to full exhalation to full inhalation, and the patient-specific motion model includes motion displacement vectors for each identified motion phase, and the identified motion phases include a plurality of phases between full inhalation and full exhalation.

* * * * *